United States Patent [19]
Khalil et al.

[11] 4,390,033
[45] Jun. 28, 1983

[54] STABLE HAIR RELAXER

[75] Inventors: Ezzat N. Khalil, Oak Park; Ali N. Syed, Hazel Crest, both of Ill.

[73] Assignee: Johnson Products Co., Inc., Chicago, Ill.

[21] Appl. No.: 294,911

[22] Filed: Aug. 25, 1981

Related U.S. Application Data

[63] Continuation-in-part of Ser. No. 202,736, Oct. 31, 1980, abandoned, which is a continuation-in-part of Ser. No. 78,593, Sep. 14, 1979, Pat. No. 4,237,910, which is a continuation-in-part of Ser. No. 34,933, Apr. 30, 1979, abandoned.

[51] Int. Cl.$^3$ .............................................. A45D 7/00
[52] U.S. Cl. ........................................ 132/7; 424/70; 424/71; 424/72
[58] Field of Search ................. 132/7; 424/72, 71, 70

[56] References Cited

U.S. PATENT DOCUMENTS

| | | | |
|---|---|---|---|
| 3,971,391 | 7/1976 | Bore et al. | 132/7 |
| 4,175,572 | 11/1979 | Hsiung et al. | 132/7 |
| 4,237,910 | 12/1980 | Khalil et al. | 132/7 |
| 4,304,244 | 12/1981 | La Guardia | 424/71 |

OTHER PUBLICATIONS

N L Industries, Inc., Product Literature, N L Industries, Chemical for Cosmetics.
N L Industries, Pigments & Chemicals, Bentone Gellants.
CFTA Cosmetic Ingredient Dictionary, 1977, p. 360.
Dark & Lovely Permanent Creme Relaxer Label, Carson Products Co., ©1978.

Primary Examiner—Dale R. Ore
Attorney, Agent, or Firm—Dressler, Goldsmith

[57] ABSTRACT

An emulsified composition is disclosed which is stable on aging and convertible to a hair relaxer composition by admixture with an aqueous solution of guanidine carbonate. The relaxer composition is comprised of a continuous water phase having dispersed therein about 3 to about 50 weight percent oleaginous material, about 7 to about 25 weight percent emulsifier and about 2 to about 30 weight percent of a lipophilic organically modified hectorite clay gellant. These compositions may be prepared by mixing and heating the oleaginous material, lipophilic hectorite gellant and less water soluble emulsifiers to about 80° C. to form the oil phase which contains no more than about 65 weight percent of the composition. Water, calcium hydroxide and emulsifiers of high water solubility are mixed and heated to form the bulk of the aqueous phase, and then added to the oil phase. After continued agitation and maintenance of about 80° C., the composition is cooled to about 50° C. and perfume is added. The mixture is mixed further, force cooled to about 25° C. and homogenized.

21 Claims, No Drawings

STABLE HAIR RELAXER

DESCRIPTION

Cross-Reference to Related Application

This is a continuation-in-part of our prior application Ser. No. 202,736 filed Oct. 31, 1980, abandoned, which is a continuation-in-part of application Ser. No. 078,593 filed Sept. 14, 1979, now U.S. Pat. No. 4,237,910, which, in turn, is a continuation-in-part of our prior application Ser. No. 034,933, filed on Apr. 30, 1979, now abandoned.

TECHNICAL FIELD

This invention relates to the straightening or relaxing of human hair.

Background Art

Aqueous alkali containing hair relaxing or straightening compositions are known in the art. Such compositions usually have a pH of about 12 to 14 due to the presence of a water-soluble alkali or alkaline material such as sodium hydroxide or guanidine, and are most frequently formulated as emulsified or creamy, viscous preparations so that once applied to the user's hair, they will not drip onto the skin or into the eyes.

Hair relaxers are generally supplied as "with base" or "no-base" formulations. A "with base" formulation is generally supplied in two packages; one containing the oleaginous base and one containing a thickened aqueous composition of alkaline materials. For these products with a base, the oleaginous base is first applied as a protective layer to the user's scalp and hair followed by application of the thickened aqueous alkaline material which then relaxes the hair. No-base formulations are one package systems in which the aqueous and oleaginous materials are co-emulsified. The no-base formulations are applied directly to the user's hair without a prior pretreatment of the scalp.

While great strides have been made in formulating no-base compositions such that proper hair shaft penetration by the alkali is achieved along with minimal scalp injury, to thereby improve safety, and also by the incorporation of conditioning agents to leave the hair with a better feel after such a treatment, most products nevertheless separate or de-emulsify on aging. The loss of stability or de-emulsification results in a product having two distinctly visible phases. While such destabilized products may be used, they must be remixed before using in an attempt to assure the user that the active ingredients are at the proper levels in the portion being used. However, such mixing, even though done thoroughly by hand, does not in fact give the user consistent results with such products. Product destabilization and resulting consumer dissatisfaction are among the chief complaints in the industry.

BRIEF SUMMARY OF THE INVENTION

A stable no-base hair relaxer composition is disclosed for use under highly alkaline conditions comprising water having dispersed therein about 3 to about 50 weight percent oleaginous material, about 7 to about 25 weight percent emulsifier and about 2 to about 30 weight of a lipophilic organically modified hectorite clay gellant.

The stable no-base hair relaxer compositions of this invention are prepared by mixing and heating the oleaginous material, lipophilic hectorite clay gellant and less water soluble emulsifiers to about 80° C. to thereby form the oil phase of the composition. Water and emulsifiers of high water solubility are mixed, heated to about 80° C. to form the bulk of the aqueous phase, and added slowly to the oil phase. After continued agitation and maintenance of the temperature at about 80° C., the composition is cooled to about 50° C. and a water-soluble, alkaline caustic material and diluting water are added. The mixture is mixed further, force cooled to about 25° C. and homogenized.

DISCLOSURE OF THE INVENTION

It has now been found that aqueous, alkaline no-base hair relaxing compositions can be formed which are stable on aging and which do not de-emulsify or separate. These compositions thereby give products whose composition of active ingredients is substantially constant throughout their lifetimes. This novel stability which is achieved in otherwise unstable formulations results from the incorporation therein of lipophilic organically modified hectorite clay gellants.

Modified hectorite (montmorillonite) clay gellants are available from N. L. Industries, Inc. in preparations designed both for use in aqueous systems (hydrophilic) and in oil dispersions (lipophilic). Those hydrophilic gellants designed for use in gelling aqueous systems include highly purified montmorillonite clays as well as hectorite clays modified with hydroxyethyl cellulose and other optional agents. Illustrative of these hydrophilic gellants are a hydroxyethyl cellulose modified hectorite clay gellant trademark named Bentone LT, an amine oxide and hydroxyethyl cellulose modified hectorite clay gellant trademark named BENAQUA as well as highly purified montmorillonite clays sold under the trademark name BEN-A-GEL and BEN-A-GEL EW.

These hydrophilic gelling agents are recommended by their manufacturer for use in a pH range of 3–11, and gellants such as Bentone LT have been used for many years to gel the aqueous, alkaline portion of "with base" relaxers which usually have pH values of about 12–13. Bentone LT was found ineffective to adequately stabilize no-base relaxer formulations.

Lipophilic hectorite clay gellants used for dispersing oils are all organically modified, and several are designated by the trademark names cited hereinbelow. The organically modified lipophilic gelling agents are modified first with a quaternary nitrogen-containing compound and then optionally, by other organic materials. Specific lipophilic gelling agents are comprised of stearalkonium hectorite or quaternium-18 [dimethyl-di-(hydrogenated tallow)-ammonium chloride]hectorite, and are sold as powders under the trademark names Bentone 27 and Bentone 38, respectively. When dispersed in organic liquids, these gelling agents are said by the manufacturer to form stable oleaginous gels and water-in-oil emulsions over a pH range of 4–10. The manufacturer also states that prolonged contact at higher or lower pH values may cause decomposition of the gelling agent with a reduction of gel strength.

Pregelled oleaginous products containing the above Bentone gellants are also commercially available and are designated by their manufacturer as mastergels. The mastergels contain about 10 percent of the above Bentone 27 or 38 gellants along with propylene carbonate and other organic liquids. It is preferred to use the commercially available mastergels as they are known in the art to be difficult to prepare.

While the lipophilic group of organically modified hectorite clay gellants are known to stabilize oil based cosmetic formulations such as eye and lip products which are formulated at or near pH 7, they are not known in the art for stabilizing aqueous emulsions under the more drastic highly, alkaline, pH 12 to 14 conditions which are used in a hair relaxer. We have found that these lipophilic gellants may be used under highly alkaline conditions from about one hundred up to about ten thousand times more basic than was thought possible by their manufacturer without apparent decomposition of the gelling agent or reduction of gel strength. This fact was surprisingly unexpected in itself, but we have also found that while these organically modified lipophilic hectorite clays were principally designed for uses at lower pH values in water-in-oil systems and for dispersing oils, they perform quite well to stabilize the oil phase of systems in which water, and not an oil forms the continuous phase as is the case of the instant no-base relaxers. This is contrary to the manufacturer's literature wherein it is stated that the Bentone 27 and 38 gellants will not thicken oil-in-water emulsions, where water is the major, or external phase. It is thought that these lipophilic, modified clay gellants prevent coalescence of the oil phase constituents while not preventing contact therebetween as is usually the case when water-in-oil emulsions are stabilized by thickening the water phase.

The preferred lipophilic hectorite clay gellants are those comprised of hectorite clays modified with (1) a quaternary nitrogen-containing compound such as stearalkonium chloride or quaternium-18 which contains at least one long chain ($C_8$–$C_{20}$) substituent on the quaternary nitrogen atom, (2) propylene carbonate, and (3) a non-polar organic liquid. Examples of such non-polar organic liquids include but are not limited to mineral spirits, mineral oil, glycerides, such as castor oil, a mixture of lanolin oil and isopropyl palmitate, and the like. [Stearalkonium chloride and quaternium-18 are defined in the CTFA Cosmetic Ingredient Dictionary, 2nd ed., published by The Cosmetic Toiletry and Fragrance Association, Inc. at pages 314 and 279, respectively.]

Specific, useful lipophilic gellants which are commercially available as mastergels include: Bentone Gel MIO, comprised of mineral oil, propylene carbonate, and quaternium-18 hectorite; Bentone Gel CAO, comprised of propylene carbonate, castor oil and stearalkonium hectorite; Bentone Gels SS71 and S130 comprised of mineral spirits (ligroin or petroleum spirits having a boiling range of about 318°–400° F.), propylene carbonate and quaternium-18 hectorite; and Bentone Gel Lantrol, comprised of propylene carbonate, a mixture of lanolin oil (dewaxed lanolin) and isopropyl palmitate, and stearalkonium hectorite. The above hectorite gellants are not only individually useful in the compositions of this invention, but may be interchanged, one for the other in a given composition, or mixed together in a composition.

The lipophilic modified hectorites may be present in the no-base hair relaxing compositions of this invention from about 2 to about 30 weight percent of the total composition. Below about 2 weight percent, little stability improvement is noted, while above about 30 weight percent, the resulting cream products tend to have congealing points which are too high to allow easy washout. Thus, using less of the hectorite material in the above range leads to softer creams while using more results in stiffer creams.

These organically modified hectorite clay gellants also provide an unexpected benefit in regard to washing the product out of the hair once hair relaxation has taken place. We have found that one may not predict the washout behavior of a no-base hair relaxer formulation simply from the fact that the product emulsion is stable in the jar. Thus, it was found that a relaxer formulation stabilized by a low molecular weight polyethylene stabilizer, which was stable in the jar inhibited contact with the hair of the caustic material by depositing an oily residue on the hair, thereby lessening the effectiveness of the product. Contrarily, when the lipophilic, organically modified hectorite clay gellants are used in the amounts discussed hereinabove, the product formulations are not only stable in the jar, but may be readily washed from the user's hair and deposit no oily residue which interferes with the action of the caustic ingredient.

About 3 to about 50 percent of the hair relaxer compositions of this invention are comprised of oleaginous materials including mineral oils, petrolatum and mineral jellies. This range is exclusive of the oleaginous materials contained in the modified hectorite clay gellants. Mineral oils useful herein have Saybolt viscosities at 100° F. ranging from about 50 S.U.S. to about 350 S.U.S. and specific gravities at 60° F. of about 0.828 to about 0.895 (0.828/0.895). The materials having Saybolt viscosities of about 50/60 S.U.S. at 100° F. and specific gravities in the ranges 0.828/0.838 at 60° F. are preferred.

Useful petrolatum is also available in several grades based upon both viscosity, melting point and color. The viscosities of these products range between about 50 and about 90 (50/90) S.U.S. at 210° F. Preferably, a colorless or "white" product having a Saybolt viscosity of about 55/75 S.U.S. at 210° F. and melting points in the range of 135°/140° F. and 127°/137° F. are used.

In addition, mineral jellies compounded of white mineral oil, petrolatum and wax may also be used as the oleaginous material in the compositions of this invention. Such materials typically have Saybolt viscosities at 210° F. of about 35/46 S.U.S. preferably about 37/40 S.U.S., U.S.P. melting points of about 97°/120° F., and pour points of about 75°/130° F., preferably of about 110°/120° F.

While the oleaginous materials may be present at about 3 to about 50 weight percent, the percentage actually used in a product depends upon the desired product consistency as is well-known in the formulation of cosmetic creams. Thus, when a very stiff relaxer is desired, petrolatum is preferred over the less viscous mineral oil and mineral jellies. While mineral jellies are themselves mixtures, mixtures such as petrolatum-mineral oil combinations are also useful for varying the viscosity or stiffness of the cream composition. When a thinner or softer cream is desired, the less viscous oleaginous materials are preferred. Additionally, since the hectorite clay gellant and oleaginous material may both be used to adjust viscosity or stiffness, one may be "played" against the other as is known in the art to obtain a desired cream viscosity.

Various emulsifying agents and mixtures thereof are present in the hair straightening formulations of this invention. These emulsifiers include non-ionic, anionic and amphoteric surfactants. Non-ionic emulsifiers may be exemplified by $C_{12}$–$C_{18}$ fatty alcohols, which may be purchased commercially as such, or individually as is the case for cetyl alcohol, pentadecanol, octadecanol and oleyl alcohol, lanolin and its polyoxyethylene derivatives such as polyoxyethylene (75) lanolin, polyethylene oxide-polypropylene oxide condensates, polyoxyethylene ethers of fatty alcohols such as polyoxyethylene (20) oleyl ether and the like. Additionally, $C_2$–$C_6$ polyhydroxy compounds such as propylene glycol, glycerin and sorbitol may be used as part of the emulsifying system. Anionic emulsifiers may be illustrated by sodium lauryl sulfate, the stearic acid anion, polyoxyethylene (3) oleyl ether phosphate, and the like. Amphoteric surfactants such as 2-heptadecyl-1-carboxymethyl-1-(2-hydroxyethyl)-2-imidazolinium chloride sold under the tradename designation Miranol DM by the Miranol Chemical Company, Inc. are particularly useful when cationic conditioning agents are also present in the formulation as is discussed hereinbelow.

The use of emulsifying agents at particular concentrations to formulate hair relaxers is known in the art. However, it has been found beneficial to use between about 7 weight percent and about 25 weight percent emulsifier in the compositions of this invention.

It is to be understood that all of the above mentioned emulsifying agents need not be used alone, nor in a single formulation, and are preferably used as combinations. When present in the formulations of the compositions of this invention, the $C_{12}$–$C_{18}$ fatty alcohols may be present from about 1 to about 20 weight percent, and preferably at about 7 to about 16 weight percent, polyoxyethylene (75) lanolin may be present at about 0.5 to about 12 weight percent, and preferably at about 1 to about 4 weight percent, lanolin itself may be present at about 1 to 5 weight percent and preferably about 2 to about 3 weight percent, polyoxyethylene (20) oleyl ether may be present at about 0.5 to about 3 weight percent, preferably at about 0.5 to about 1.5 weight percent, and the $C_2$–$C_6$ polyhydroxy compounds may be present at about 0.5 to about 10 weight percent, preferably at about 1 to about 6 weight percent, all based upon the total weight of the composition.

When compounding the compositions of this invention, the oleaginous material and nonionic emulsifiers comprise the oil phase of the cream. Those nonionic emulsifiers which are relatively more water soluble, such as polyoxyethylene (75) lanolin, the $C_2$–$C_6$ polyhydroxy compounds such as propylene glycol, and polyoxyethylene (20) oleyl ether may also be used in the aqueous phase of the relaxer cream.

Of the anionic emulsifiers, polyoxyethylene (3) oleyl ether phosphate may be present at about 0.05 to about 3 weight percent, stearic acid (added as the acid and neutralized in situ) may be present at about 0.1 to about 1 weight percent and preferably at about 0.2 to about 0.6 weight percent, and sodium lauryl sulfate may be present at about 0.2 to about 2 weight percent, preferably at about 0.3 to 1.75 weight percent of the total mixture.

The preferred amphoteric emulsifier, 2-heptadecyl-1-carboxymethyl-1-(2-hydroxyethyl)-2-imidazolinium chloride may be present from about 0.25 to about 10 weight percent and preferably at about 0.25 to about 5 weight percent of the total composition. This amphoteric emulsifier is particularly useful for hair relaxing compositions which also condition the hair, leaving it soft and managable as well as straightening it. Water-soluble, quaternary, cationic polymers which modify the hair surface characteristics and thereby improve the hair feel and ease of combing may be used as such hair conditioners or conditioning agents.

The co-assigned U.S. Pat. No. 4,175,572, issued Nov. 17, 1979, discloses hair conditioning compositions which may be used in conjunction with highly alkaline hair waving or straightening compositions based on sodium hydroxide. The conditioner described therein may be combined with the waving or relaxing formulation prior to use, or can be applied separately to the hair either before or after application of the relaxer or the waving composition. The compositions therein disclosed contain a conditioning agent comprised of a cationic quaternary nitrogencontaining polymer believed to have recurring units of the formula:

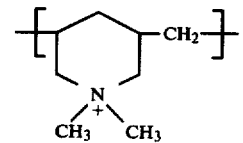

It has now been found that no-base relaxer compositions may be prepared which comprise the above described amphoteric emulsifier and conditioning cationic polymer as well as an organically modified, lipophilic hectorite gellant to provide a unitary product which relaxes the hair and conditions it while maintaining compositional stability and therefore shelf life. These stable conditioning no-base relaxers have compositions similar to those described hereinabove with the exception that the polymers having the above-described recurring unit formulae are also present at about 0.05 to about 8 weight percent and preferably about 0.5 to about 2 weight percent along with the above-described amphoteric emulsifier.

Homopolymers having the above shown recurring units are preferred conditioning agents. These polymers may be prepared by polymerizing diallyldimethylammonium chloride or bromide, or other suitable diallyldimethylammonium salts, using a free radical generating polymerization catalyst, such as a peroxide or hydroperoxide, then employing a suitable an ion exchange resin, if desired, according to the methods described in U.S. Pat. Nos. 3,288,770 and 3,412,091. The resulting polymers are polydiallyldimethylammonium salts, such as polydiallyldimethylammonium chloride.

The hair relaxing compositions also contain a water-soluble alkaline caustic material which is capable of bringing the pH of the composition to a value of about 12 to 14. Alkali metal hydroxides, including sodium hydroxide, potassium hydroxide and lithium hydroxide may be used as the water-soluble alkaline caustic material. Sodium hydroxide is the preferred alkali metal hydroxide and may be present in amounts from about 1 to 4.5 weight percent of the total composition, preferably from about 1.3 to about 3.5 weight percent.

The water-soluble alkaline caustic material may also be a strong organic base, such as guanidine, preferably made just before application of the composition to the hair by the reaction of guanidine carbonate with calcium hydroxide. In this embodiment, calcium hydroxide usually replaces sodium hydroxide in the emulsified composition, and guanidine carbonate, in a separate aqueous solution, is combind with the emulsion just before use. Alternatively, the guanidine carbonate may be included in the emulsion and calcium hydroxide added just before use in an aqueous suspension. Other alkaline earth hydroxides, such as barium or strontium hydroxide may be used in place of calcium hydroxide to release free guanidine from guanidine carbonate. Alkaline earth oxides may also be used, producing hydroxides when added to water.

The amount of guanidine in the final composition is from about 0.05 to 0.8 molar, preferably from about 0.4 to 0.6 molar. Guanidine concentrations within this range are obtained from guanidine carbonate concentrations in the final mixture between about 0.031 and 0.38 molar and calcium hydroxide concentrations in the final mixture between about 0.025 and 2.2 molar. In the emulsified composition prior to the addition of aqueous guanidine carbonate, the amount of calcium hydroxide is generally between about 0.25 and 20 weight percent, and preferably between about 5 and 10 weight percent.

Other organic bases may be used in place of guanidine, including N-methyl guanidine, dimethylaminoguanidine (sym. and asym.), acetamidine, dimethylaminoamidine, aminoamidine, and acetamide. The organic base may be liberated from salts other than the carbonate salt, such as from a sulfate or sulfite salt. In general, the emulsified composition may contain a water soluble salt of a strong organic base with an anion capable of being precipitated by an alkaline earth metal ion under alkaline conditions.

Water, the amphoteric and anionic emulsifiers (except stearic acid), the alkali or alkaline earth hydroxide and the above mentioned relatively more water-soluble nonionic emulsifiers generally comprise the aqueous phase of the relaxer creams during compounding. The term "highly alkaline" is used herein to denote a composition having a pH value of about 12 to about 14.

While stable no-base relaxer formulations or compositions of this invention may be prepared within the above-mentioned ranges of component amounts, three groups of compositions comprised of differing amounts of the various components are particularly preferred. These compositions may be conveniently classed as those containing relatively large amounts of water and alkali, those which contain relatively small amounts of water and alkali, and those which contain hair conditioning agents and which may be termed conditioning relaxers. Water forms the continuous phase of each of these groups of compositions, even in those relaxer compositions where water is present at only about 35 percent by weight of the composition. The non-water components, i.e., oleaginous material, emulsifier and gellant, of all these compositions make up no more than about 65 percent by weight of the compositions.

The stable relaxers containing relatively large amounts of water and alkali are those which are comprised of about 60 to about 75 weight percent water, about 4 to about 8 weight percent oleaginous material, preferably petrolatum, about 8 to about 12 weight percent of a lipophilic hectorite gellant and about 2.5 to about 3.5 weight percent sodium hydroxide (or from about 5 to about 20 weight percent calcium hydroxide) along with about 10 to about 20 weight percent emulsifier. A useful emulsifier for such a system includes about 9 to about 16 weight per unit $C_{12}$–$C_{18}$ fatty alcohol, about 0.5 to about 2 weight percent polyoxyethylene (75) lanolin and about 0.5 to about 2 weight percent sodium lauryl sulfate.

Those relaxers having relatively small amounts of water and alkali are comprised of about 35 to about 45 weight percent water. Additionally, these compositions may be comprised of about 25 to about 35 weight percent oleaginous material, preferably mineral jelly, about 8 to about 20 weight percent lipophilic hectorite gellant, and about 1.3 to about 2.5 weight percent sodium hydroxide (or about 3 to about 5 weight percent calcium hydroxide) along with about 12 to about 20 weight percent emulsifier. A useful emulsifier in such a composition may be comprised of about 7 to about 14 weight percent $C_{12}$–$C_{18}$ fatty alcohols, about 0.2 to about 0.6 weight percent stearic acid, about 2 to about 3 weight percent lanolin, about 2 to about 3 weight percent polyoxyethylene (75) lanolin, about 0.5 to about 1.5 weight percent polyoxyethylene (20) oleyl ether phosphate and about 0.25 to about 1 weight percent sodium lauryl sulfate.

In addition to the range of ingredients previously disclosed, compositions containing alkaline earth hydroxides, such as about 5 to about 10 weight percent calcium hydroxide, and organic bases, such as about 0.05 to about 0.8 molar guanidine added as guanidine carbonate, more preferably contain about 20 to about 45 percent water, about 15 to about 25 weight percent oleaginous material, preferably a petrolatum-mineral oil mixture containing at least about 80 weight percent petrolatum, about 8 to about 20 weight percent lipophilic hectorite gellant and about 15 to about 25 weight percent emulsifier. A useful emulsifier for such compositions is typically comprised of about 7 to about 16 weight percent $C_{12}$–$C_{18}$ fatty alcohols, about 0.05 to about 1.5 weight percent polyoxyethylene (20) oleyl ether phosphate, about 0.5 to about 12 weight percent polyoxyethylene (75) lanolin, and about 1 to about 10 weight percent propylene glycol. Particularly preferred compositions also include about 0.05 to about 8 weight percent polydiallydimethylammonium salt, and about 0.25 to about 10 weight percent 2-heptdecyl-1-carboxymethyl-1(2-hydroxyethyl)-2-imidazolinium chloride. In still more particularly preferred compositions, the polydiallydimethylammonium salt is present at about 0.5 weight percent, and the preferred amphoteric emulsifier is present at about 0.25 to about 5 weight percent.

The stable aqueous, lipophilic hectorite gellant containing conditioning relaxer of this invention may be formulated to comprise a broad range of ingredients. While each of the above mentioned oleaginous materials may be used alone, it has been found preferable to use about 10 to about 50 weight percent of materials such as mineral jellies and petrolatum-mineral oil mixtures. It is preferred to use a mixture of about 5 to about 30 weight percent petrolatum and about 3 to about 20 weight percent mineral oil. Most preferred formulations are comprised of about 15 to about 25 weight percent petrolatum and about 5 to about 15 weight percent mineral oil. About 2.5 to about 30 weight percent of a lipophilic hectorite gellant, preferably about 10 to about 20 weight percent, and about 1 to about 3 weight percent sodium hydroxide (or about 0.5 to 20 weight percent calcium hydroxide) are included, as well as about 10 to about 25 weight percent of the emulsifier.

Included in the emulsifier is about 0.25 to about 10 weight percent, and preferably about 0.25 to about 5 weight percent, 2-heptadecyl-1-carboxymethyl-1-(2-hydroxyethyl)-2-imidazolinium chloride which is known for its ability to reduce buildup caused by cationic conditioning agents. Additionally, the emulsifier may be comprised of about 1 to about 20 weight percent $C_{12}$–$C_{18}$ fatty alcohols, about 0.05 to about 3 weight percent polyoxyethylene (3) oleyl ether phosphate and about 0.5 to about 12 weight percent polyoxyethylene (75) lanolin. About 1 to about 6 weight percent propylene glycol may also be added.

The preferred polymeric conditioning agent in such compositions is the quaternary nitrogen-containing polymer as discussed hereinabove. As already stated, this conditioning polymer may be used at about 0.05 to about 8 weight percent of the compositions, and preferably at about 0.5 to about 2 weight percent.

In addition to the above constituents, adjuvants such as perfume, menthol and proteinacious materials such as commercially available hydrolyzed protein polypeptides may be added to the formulation to lend their own cosmetic effects.

To prepare the novel no-base relaxers of this invention other than those containing conditioning agents, the oleaginous material and hectorite gellant are heated together to about 80° C. with agitation until a substantially uniform dispersion results. The emulsifying agents of low water solubility, such as $C_{12}$–$C_{18}$ fatty alcohols, lanolin, stearic acid and the like are then added with continued agitation and maintenance of the temperature at about 80° C. This mixture becomes the oil phase of the composition.

The emulsifiers of high water solubility such as sodium lauryl sulfate, polyoxyethylene (75) lanolin, polyoxyethylene (20) oleyl ether, propylene glycol and the like are generally added to deionized water and the admixture heated to about 80° C. with stirring. This mixture comprises the bulk portion of the aqueous phase of the composition.

The above bulk portion of the aqueous phase is then slowly added with agitation to the oil phase and agitation is continued thereafter for about 15 minutes. The agitated mixture is then cooled to about 50° C. at which temperature aqueous sodium hydroxide (50 weight percent solution), adjuvants, perfume and the like are added and the mixture diluted to its final volume with deionized water. The mixture is then stirred for about an additional 15 minutes and then force cooled to about ambient (25° C.). On reaching ambient temperature, the mixture is homogenized by conventional techniques, such as by use of ultrasonic equipment.

Preparation of the conditioning, hectorite gel containing relaxers is similar to that described hereinabove, with the exception being that the conditioning, quaternary nitrogen-containing polymer and amphoteric emulsifier are added to the bulk portion of the aqueous phase and dispersed therein prior to addition and admixture of the aqueous phase bulk portion into the oil phase.

When using the stable hair relaxers of this invention, it is preferable that the person on whose head the compositions will be used (the model) not wash her (or his) hair for at least 24 hours prior to the relaxer treatment. This preference stems from the scalp protecting effect produced by the model's own sebum secretions. In addition, while washing the hair, slight physical damage can occur to the scalp which can become aggravated by the alkali in the relaxer.

The model's hair is divided into four portions as delineated by the areas separated when hypothetical lines are drawn from ear-to-ear and from nose-to-backbone. Starting with the rear portions, the relaxer cream is applied to the hair with the back or smooth side of a comb (opposite from the teeth). Care is taken to avoid putting the composition on the scalp and about ⅛-¼" of the root end (lower portion) of the hair shafts. This process takes about 8 minutes for treatment of all the model's hair.

Each portion of the hair is then physically smoothed with the comb back. At this time in the treatment, the scalp and lower portions of the hair shafts are contacted with the relaxer cream. The smoothing step helps to ensure hair shaft penetration by the relaxer and also puts tension on the hair to help in straightening the hair. The smoothing step is then repeated. The total time for smoothing (both initial and repeat steps) normally takes from about 5 to about 10 minutes, depending upon the hair length, thickness and length. Thus, at this point, the relaxer is on the head for about 13 to about 18 minutes.

The relaxer is then thoroughly and rapidly rinsed from the hair using water having a temperature of about 37° C. The rinsing step is followed by a shampooing with a non-alkaline shampoo. The shampoo is preferably buffered on the acid side of neutral at about pH 4 to 5 so that residual alkali left in the hair or on the scalp may be neutralized. This shampooing is usually repeated two to three times.

After shampooing, the hair may be treated with a conditioner to improve wet combing and hair feel. When the conditioning relaxers of this invention are used, no extra conditioning step is needed. The hair may then be set and dried in a desired coiffure as is known in the art.

When guanidine is the water soluble alkali material and the emulsified composition contains calcium hyroxide, or another alkaline earth hydroxide, it is necessary to blend the emulsified composition, just before application to the hair, with an activator solution comprising an aqueous solution of guanidine carbonate, preferably containing a small amount of a thickener. The emulsified compositions are blended in proportions producing free guanidine in an amount within the limits disclosed above.

BEST MODES FOR CARRYING OUT THE INVENTION

EXAMPLES 1–3: Stable Hair Relaxer With High Water and Alkali Content

| Components | Examples (weight % of total Relaxer) | | |
|---|---|---|---|
| | 1 | 2 | 3 |
| Petrolatum (Note 1) | 5 | 6 | 7 |
| Modified hectorite clay gellant (Note 2) | 9 | 10 | 11 |
| $C_{12}$–$C_{18}$ fatty alcohol (Note 3) | 10 | 11 | 12 |
| Deionized water | 60 | 60 | 55 |
| Sodium lauryl sulfate | 1.5 | 1.5 | 1.5 |
| Polyoxyethylene (75) lanolin | 1.5 | 1.5 | 1.5 |
| Sodium hydroxide (50% by weight NaOH in deionized water) | 3.10 (6.2 | 3.22 6.44 | 3.35 6.7 total composition addition.) |
| perfume | 0.2 | 0.2 | 0.2 |
| Deionized water (Q.S. | 6.6 | 3.36 | 5.1 |

-continued

|  | Examples (weight % of total Relaxer) | | |
|---|---|---|---|
| Components | 1 | 2 | 3 |
| to 100%) | | | |

Note 1. Petrolatum having a U.S.P. melting point of 135/140° F. and a Saybolt viscosity at 210° F. of 55/75 S.U.S. is used.
Note 2. A modified hectorite clay gellant sold by N.L. Industries, Inc. under the trademark designations Bentone Gel MIO, Bentone Gel CAO, Bentone Gel SS71, Bentone Gel S130 and Bentone Gel Lantrol may be used.
Note 3. Equal weights of cetyl alcohol and oleyl alcohol are used.

Petrolatum and modified clay gellant are placed in a heatable container equipped with a propeller-type mixer, heated to a temperature of about 80° C. and mixed until a substantially uniform dispersion is achieved. The fatty alcohol is added thereto while maintaining said temperature and the resulting admixture mixed until the dispersion is substantially uniform, to thereby form the oil phase.

Deionized water is added to a separate heatable container also provided with a mixer, and sodium lauryl sulfate, polyoxyethylene (75) lanolin are added thereto. This admixture is heated with mixing to a temperature of about 80° C. to thereby form the bulk portion of the aqueous phase.

The bulk of the aqueous phase is then added with mixing to the oil phase at a temperature of about 80° C. over 15 minutes. The resulting admixture is then cooled to about 50° C. with continued agitation and sodium hydroxide, perfume and the remaining water added thereto. This admixture is then further mixed for 15 minutes and then force cooled to 25° C. (ambient). The cooled composition is then homogenized.

The hair relaxers of Examples 1–3 relax hair, are stable and do not separate into two visible phases on accelerated aging.

EXAMPLES 4–6: Stable Hair Relaxers With Low Water and Alkali Content

|  | Examples (weight % of total Relaxer) | | |
|---|---|---|---|
| Components | 4 | 5 | 6 |
| Mineral jelly (Note 4) | 27 | 31 | 33 |
| Modified hectorite clay gellant (Note 2 above) | 17 | 11 | 9 |
| C$_{12}$–C$_{18}$ fatty alcohols (Note 3 above) | 13 | 11 | 8 |
| Lanolin | 2 | 2.5 | 3 |
| Stearic acid | 0.4 | 0.4 | 0.4 |
| Deionized water | 30 | 30 | 30 |
| Polyoxyethylene (75) lanolin | 2.5 | 2.5 | 2.5 |
| Polyoxyethylene (20) oleyl ether | 1.3 | 1.0 | 0.8 |
| Sodium lauryl sulfate | 0.5 | 0.5 | 0.5 |
| Sodium hydroxide (50% by weight NaOH in deionized water) | 1.67 (3.34 total composition addition) | 2.0 4.0 | 2.2 4.4 |
| Perfume | 0.02 | 0.02 | 0.02 |
| Menthol | 0.2 | 0.2 | 0.2 |
| Hydrolyzed Animal protein solution (Note 5) (about 50% active) | 0.25 (0.50 total composition addition) | 0.25 0.50 | 0.25 0.50 |
| Deionized water | 2.24 | 5.38 | 7.68 |

-continued

|  | Examples (weight % of total Relaxer) | | |
|---|---|---|---|
| Components | 4 | 5 | 6 |
| (Q.S. to 100%) | | | |

Note 4. Mineral jelly having a Saybolt viscosity of 38/40 S.U.S. at 210° F., a melting point of 111°/116° F. and pour point of 110°/120° F. is used. This material is commercially available under the designation "Mineral Jelly No. 20" from the Penreco Division of Penzoil Company.
Note 5. A hydrolyzed animal protein having 48–50 weight percent total solids, a hydroxy proline content of about 5–7 weight percent and an average molecular weight of 800–1000 available from Stepan Chemical Company under the designation "Polypeptide 37" is used.

Mineral jelly and modified hectorite gellant are placed in a heatable container equipped with a mixer, heated to a temperature of about 80° C. and mixed until a substantially uniform dispersion is achieved. The fatty alcohols, lanolin and stearic acid are added thereto with continued agitation and maintenance of said temperature until the dispersion is substantially complete, to thereby form the oil phase of the composition.

Deionized water is placed in a separate, heatable container equipped with an agitator and polyoxyethylene (75) lanolin, polyoxyethylene (20) oleyl ether and sodium lauryl sulfate are added thereto. This admixture is mixed and heated to about 80° C. to form the bulk portion of the aqueous phase.

The bulk portion of the aqueous phase is added to the above oil phase with agitation at about 80° C. over a period of 15 minutes. The resultant admixture is cooled to 50° C. with continued agitation and sodium hydroxide, perfume, menthol, a solution of hydrolyzed animal protein and the remaining deionized water are added. This admixture is then mixed for about 25 minutes and force cooled to 25° C. It is then homogenized.

The hair relaxer compositions of Examples 4–6 relax or straighten hair, are stable and do not separate into two visible phases on accellerated aging.

EXAMPLES 7–9: Stable Conditioning Hair Relaxers

|  | Examples (weight % of total Relaxer) | | |
|---|---|---|---|
| Components | 7 | 8 | 9 |
| Petrolatum (Note 1 above) | 20 | 20 | 20 |
| Mineral Oil (Note 6) | 5 | 14 | 5 |
| Modified hectorite clay gellant (Note 2 above) | 15 | 10 | 15 |
| C$_{12}$–C$_{18}$ fatty alcohols (Note 3 above) | 7 | 7 | 7 |
| Polyoxyethylene (3) oleyl ether phosphate | 0.25 | 0.25 | 0.25 |
| Deionized water | 36.01 | 35.71 | 35.71 |
| 2-heptadecyl-1-carboxymethyl-1-(2-hydroxyethyl)-2-imidazolinium chloride (Note 7) (20% active, aqueous paste) | 0.37 (1.84 total composition addition) | 0.37 1.84 | 0.37 1.84 |
| Polymeric quaternary nitrogen-conditioning agent (Note 8) (about 40% solids in water) | 1.0 (2.5 total composition addition) | 1.0 2.5 | 1.0 2.5 |
| Polyoxyethylene (75) lanolin | 3 | 3 | 3 |

-continued

| | Examples (weight % of total Relaxer) | | |
|---|---|---|---|
| Components | 7 | 8 | 9 |
| Propylene glycol | 5 | 1 | 5 |
| Sodium hydroxide (50% by weight aqueous solution) | 2.05 (4.1 | 2.2 4.4 | 2.2 4.4 |
| | total composition addition) | | |
| Perfume | 0.3 | 0.3 | 0.3 |

Note 6. This mineral oil has a Saybolt viscosity at 100° F. of 50/60 S.U.S. and a specific gravity in the range of 0.828/0.838 at 60° F.
Note 7. Available from the Miranol Chemical Company, Inc. under the trademark designation Miranol DM.
Note 8. A water soluble quaternary nitrogen-containing polymer available from Merck & Co., Inc. under the trademark designation Merquat 100 and which is thought to have recurring units of the formula:

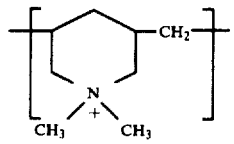

Petrolatum, mineral oil and modified, lipophilic hectorite clay gellant are placed in a heatable container equipped with an agitator, heated to a temperature of about 80° C. and mixed until a substantially uniform dispersion is achieved. Fatty alcohols and polyoxyethylene (3) oleyl ether phosphate are added thereto with agitation while maintaining said temperature. This admixture is agitated until a substantially uniform dispersion is achieved to thereby produce the oil phase of the composition.

In a separate heatable container equipped with a mixer, are added: deionized water, 2-heptadecyl-1-carboxymethyl-1-(2-hydroxyethyl)-2-imidazolinium chloride (amphoteric emulsifier), the polymeric quaternary nitrogen-containing agent, propylene glycol and polyoxyethylene (75) lanolin. This admixture is mixed and heated to a temperature of about 80° C. to form the bulk portion of the aqueous phase.

The bulk portion of the aqueous phase is then added to the oil phase with stirring at a temperature of 80° C. over a period of 15 minutes. The resultant admixture is mixed for an additional 15 minutes and then cooled to 50° C. Sodium hydroxide, perfume and the requisite amount of deionized water are then added, and the composition mixed for an additional 15 minutes, force cooled to 25° C. and homogenized.

The hair relaxer compositions of Examples 7-9 relax or straighten hair, and are not only stable on aging and do not separate into two visible phases, but also condition the hair and provide the hair with a better feel and combing properties after the relaxer treatment without the need for an additional conditioner treatment.

EXAMPLES 10-14: Stable Hair Relaxers Based on Guanidine

| | Examples (Weight Percent Of Emulsified Composition) | | |
|---|---|---|---|
| Components | 10 | 11 and 12 | 13 and 14 |
| Petrolatum Note 1 Above | 20.00 | 20.00 | 20.00 |
| Mineral Oil (Note 6 above) | 0.90 | 0.90 | 0.90 |
| $C_{12}$-$C_{18}$ fatty Alcohols (Note 3 above) | 10.00 | 10.00 | 10.00 |
| Modified hectorite clay gellant | 15.00 | 15.00 | 15.00 |
| (Note 2 above) | | | |
| Polyoxyethylene (3) oleyl ether phosphate | 0.10 | 0.10 | 0.10 |
| Deionized Water | 33.99 | 19.99 | 39.49 |
| Calcium Hydroxide | 6.00 | 20.00 | 0.50 |
| Polymeric quaternary nitrogen conditioning agent (Note 8 above) (about 40% solids in water) | 1.32 (3.30 | 1.32 3.30 | 1.32 3.30 |
| | total composition addition) | | |
| Polyoxyethylene (75) lanolin | 3.71 | 3.71 | 3.71 |
| 2-heptadecyl-1-carboxymethyl-1-(2-hydroxyethyl)-2-imidazolimium chloride (Note 7 above) (20% active, aqueous paste) | 1.50 | 1.50 | 1.50 |
| Propylene glycol | 5.50 | 5.50 | 5.50 |

Petrolatum, mineral oil and modified lipophilic hectorite clay gellant are placed in a heatable container equipped with an agitator, heated to a temperature of about 80° C. and mixed until a substantially uniform dispersion is achieved. Fatty alcohols and polyoxyethylene (3) oleyl ether phosphate are added thereto with agitation while maintaining said temperature. This admixture is agitated until a substantially uniform dispersion is achieved to thereby produce the oil phase of the composition.

In a separate heatable container equipped with a mixer, are added: deionized water, calcium hydroxide, 2-heptadecyl-1-carboxymethyl-1-(2hydroxyethyl)-2-imidazolinium chloride (amphoteric emulsifier), the polymeric quaternary nitrogen-containing conditioning agents, propylene glycol and polyoxyethylene (75) lanolin. This admixture is mixed and heated to a temperature of about 80° C. to form the bulk portion of the aqueous phase.

The bulk portion of the aqueous phase is then added to the oil phase with stirring at a temperature of 80° C. over a period of 15 minutes. The resultant admixture is mixed for an additional 15 minutes and then cooled to 50° C. Perfume and the requisite amount of deionized water are then added, and the composition mixed for an additional 15 minutes, force cooled to 25° C. and homogenized.

An aqueous solution of guanidine carbonate was prepared containing 25.00 weight percent of guanidine carbonate, 0.25 weight percent of sodium alginate and 74.75 weight percent of water. 25 parts by weight of this solution was added to 106.3 parts of the emulsified composition of Example 10 with stirring to make up the final composition of Example 10.

40 parts by weight and 5 parts by weight of the guanidine carbonate solution were added to separate 106.3 part portions of the emulsified composition of Examples 11 and 12 to make up the final Example 11 and Example 12 compositions respectively.

40 parts by weight and 5 parts by weight of the guanidine carbonate solution were added to separate 106.3 part portions of the emulsified compositions of Examples 13 and 14 to make up the final Examples 13 and 14 compositions respectively.

All of the compositions of Examples 10 to 14 relax hair acceptably, with Example 10 preferred.

The invention is defined by the claims which follow.

What is claimed is:

1. In a no base hair relaxer composition comprising a continuous water phase having dispersed therein about 3 to about 50 weight percent oleaginous material, about 7 to about 25 percent by weight emulsifier and containing a water soluble organic base in sufficient quantity to provide a pH of said composition at about 12–14, wherein the improvement comprises said composition being stabilized against phase separation by about 2 to about 30 weight percent lipophilic, organically modified hectorite clay gellant comprised of hectorite modified with a quaternized nitrogen-containing compound containing at least one $C_8$–$C_{20}$ long chain substituent on the quaternary nitrogen atom, propylene carbonate and an organic liquid, said weight percents being based upon the total weight of the composition, said oleaginous material, emulsifier and gellant together comprising no more than about 65 percent by weight of the composition.

2. The no base hair relaxer composition of claim 1 wherein said organic base is guanidine and is prepared just before use of said composition by the reaction of calcium hydroxide and guanidine carbonate.

3. In an emulsified composition suitable as a component of a no base hair relaxer composition and comprising a continuous water phase having dispersed therein about 3 to about 50 weight percent oleaginous material, about 7 to about 25 percent by weight emulsifier and containing a sufficient amount of an alkaline earth hydroxide to produce a pH between about 12 and about 14 when said composition is blended with an aqueous solution of the salt of a strong organic base with an anion capable of being precipitated by the ion of said alkaline earth, wherein the improvement comprises said composition being stabilized against phase separation by about 2 to about 30 weight percent lipophilic, organically modified hectorite clay gellant comprised of hectorite modified with a quaternized nitrogen containing compound containing at least one $C_8$–$C_{20}$ long chain substituent on the quaternary nitrogen atom, propylene carbonate and an organic liquid, said weight percents being based upon the total weight of the composition, said oleaginous material, emulsifier and gellant together comprising no more than about 65 percent by weight of the composition.

4. The composition of claim 3 wherein said alkaline earth hydroxide is present in an amount from about 0.5 weight percent to about 20 weight percent of said emulsified composition.

5. The hair relaxer of claim 4 wherein said oleaginous material is selected from the group consisting of petrolatum, mineral jelly and mineral oil and mixtures thereof.

6. The hair relaxer of claim 4 wherein said emulsifier is selected from the group consisting of anionic, amphoteric and non-ionic emulsifiers and mixtures thereof.

7. The hair relaxer of claim 4 wherein said quaternized nitrogen-containing compound is selected from the group consisting of stearalkonium chloride and dimethyl-di-(hydrogenated tallow)ammonium chloride and said organic liquid is selected from the group consisting of mineral oil, castor oil, mineral spirits, and a mixture of lanolin oil and isopropyl palmitate.

8. The hair relaxer of claim 4 wherein said emulsifier comprises about 0.25 to about 10 weight percent 2-heptadecyl-1-carboxymethyl-1-(2-hydroxyethyl)-2-imidazolinium chloride and about 0.05 to about 8 weight percent of a quaternary polymer prepared by polymerizing a diallyldimethylammonium salt.

9. In a no-base hair relaxer composition comprising a continuous water phase having dispersed therein
about 3 to about 50 weight percent oleaginous material selected from the group consisting of petrolatum, mineral jelly and mineral oil;
about 7 to about 25 weight percent emulsifier selected from the group consisting of anionic, amphoteric and non-ionic emulsifiers; about 0.25 to about 20 weight percent of calcium hydroxide, said composition having a pH of about 12 to about 14 when blended with an aqueous solution of guanidine carbonate; wherein the improvement comprises said composition being stabilized against phase separation by about 2 to about 30 weight percent of a lipophilic modified hectorite clay gellant comprised of hectorite modified by propylene carbonate, a quaternized nitrogen containing compound selected from the group consisting of stearalkonium chloride and dimethyl-di-(hydrogenated tallow) ammonium chloride and an organic liquid selected from the group consisting of mineral oil, castor oil, mineral spirits and a mixture of lanolin and isopropyl palmitate;
said weight percents being based upon the total weight of said composition, and said oleaginous material, emulsifier and gellant together comprising no more than about 65 weight percent of said composition.

10. The hair relaxer of claim 9 wherein
said oleaginous material is present at about 15 to about 25 weight percent and is a petrolatum-mineral oil mixture containing at least about 80 weight percent petrolatum;
said lipophilic hectorite gellant is present at about 8 to about 20 weight percent; and
said calcium hydroxide is present at about 5 to about 10 weight percent.

11. The hair relaxer of claim 10 wherein said emulsifier is comprised of about 7 to about 16 weight percent $C_{12}$–$C_{18}$ fatty alcohols, about 0.5 to about 12 weight percent polyoxyethylene (75) lanolin, about 0.05 to about 1.5 weight percent polyoxyethylene (20) oleyl ether phosphate, and about 1 to about 10 weight percent propylene glycol.

12. The hair relaxer of claim 9 additionally comprising about 0.5 to about 2 weight percent of a quaternary homopolymer prepared by polymerizing a diallyldimethylammonium salt.

13. The hair relaxer of claim 12 wherein
said oleaginous material comprises a petrolatum-mineral oil mixture containing at least about 80 weight percent petrolatum and is present at about 15 to about 25 weight percent;
said calcium hydroxide is present at about 5 to about 10 weight percent; and
said emulsifier comprises about 0.25 to about 5 weight percent 2-heptadecyl-1-carboxymethyl-1-(2-hydroxyethyl)-2-imidazolinium chloride.

14. The hair relaxer of claim 13 wherein said emulsifier comprises about 7 to about 16 weight percent $C_{12}$–$C_{18}$ fatty alcohols, about 0.05 to about 1.5 weight percent polyoxyethylene (3) oleyl ether phosphate, about 1 to about 10 weight percent propylene glycol, and about 0.5 to about 12 weight percent polyoxyethylene (75) lanolin.

15. A method of preparing an emulsified composition stable against phase separation and capable of producing a hair relaxer upon admixture with an aqueous solution of guanidine carbonate comprising the steps of:
  (A) heating and agitating a mixture of about 3 to about 50 weight percent of an oleaginous material and about 2 to about 30 weight percent of lipophilic modified hectorite clay gellant comprised of hectorite modified with a quaternized nitrogen-containing compound containing at least one $C_8$–$C_{20}$ long chain substituent on the quaternary nitrogen atom at about 80° C. until a substantially uniform dispersion results, said weight percents being based upon the total weight of the composition;
  (B) admixing emulsifying agents of low water solubility thereto while maintaining said agitation and temperature to thereby form the oil phase of said composition;
  (C) heating and agitating water, calcium hydroxide and emulsifiers of high water solubility in a separate container at about 80° C. to thereby form the bulk of the aqueous phase of said composition, all of said emulsifiers comprising about 7 to about 25 weight percent of said composition; and said emulsifiers, oleaginous material and gellant together comprising no more than about 65 percent by weight of said composition;
  (D) slowly admixing said bulk of the aqueous phase into said oil phase at about 80° C.;
  (E) thereafter mixing said admixture for about 15 minutes;
  (F) cooling said admixture to about 50° C. and adding perfume;
  (G) thereafter mixing said composition for about 15 minutes, and then force cooling said composition to about 25° C.; and
  H. homogenizing said cooled composition.

16. The method of claim 15 wherein
  said oleaginous material is selected from the group consisting of mineral oil, petrolatum and mineral jelly and mixtures thereof;
  said lipophilic modified hectorite clay gellant is a hectorite modified with propylene carbonate, a quaternized nitrogen-containing compound selected from the group consisting of stearalkonium chloride and dimethyl-di-(hydrogenated tallow)-ammonium chloride, and an organic liquid selected from the group consisting of mineral oil, castor oil, mineral spirits and a mixture of lanolin oil and isopropyl palmitate; and
  said emulsifiers are selected from the group consisting of anionic, amphoteric and non-ionic emulsifiers and mixtures thereof.

17. The method of claim 15 wherein the bulk of said aqueous phase comprises
  about 0.25 to about 10 weight percent 2-heptadecyl-carboxymethyl-1-(2-hydroxyethyl)-2-imidazolinium chloride; and
  about 0.05 to about 8 weight percent of a quaternary polymer prepared by polymerizing a diallyldimethylammonium salt.

18. A method of preparing an emulsified composition stable against phase separation and capable of producing a hair relaxer upon admixture with an aqueous solution of guanidine carbonate comprising the steps of:
  (A) heating and agitating a mixture of about 3 to about 50 weight percent of an oleaginous material selected from the group consisting of petrolatum, mineral oil and mineral jelly, and about 2 to about 30 weight percent lipophilic modified hectorite clay gellant comprising hectorite modified with propylene carbonate, a quaternized nitrogen-containing compound selected from the group consisting of stearalkonium chloride and dimethyl-di-(hydrogenated tallow)ammonium chloride, and an organic liquid selected from the group consisting of mineral oil, castor oil, mineral spirits and a mixture of lanolin oil and isopropyl palmitate, at about 80° C. until a substantially uniform dispersion results, said weight percents being based upon the weight of said composition.
  (B) admixing emulsifying agents of low water solubility thereto while maintaining said agitation and temperature to thereby form the oil phase of said composition;
  (C) heating and agitating water, calcium hydroxide and emulsifiers of high water solubility in a separate container at about 80° C. to thereby form the bulk portion of the aqueous phase of said composition, all of said emulsifiers comprising about 7 to about 25 weight percent of said composition, and being selected from the group consisting of anionic, amphoteric and non-ionic emulsifiers, said emulsifiers, oleaginous material and gellant together comprising no more than about 65 weight percent of said composition;
  (D) slowly admixing said bulk portion of the aqueous phase into said oil phase at about 80° C.;
  (E) thereafter mixing said admixture for about 15 minutes;
  (F) cooling said admixture to about 50° C. and adding perfume;
  (G) thereafter mixing said composition for about 15 minutes, and then force cooling said composition to about 25° C.; and
  (H) homogenizing said cooled composition.

19. The method of claim 18 wherein said emulsifier of high water solubility includes about 0.25 to about 5 weight percent 2-heptadecyl-1-carboxymethyl-1-(2-hydroxyethyl)-2-imidazolinium chloride and said composition is also comprised of about 0.5 to about 2 weight percent of a quaternary polymer prepared by polymerizing a diallyldimethylammonium salt.

20. In the method of treating human hair with a no-base relaxer composition in which the relaxer is applied to the hair, the hair physically smoothed, rinsed, shampooed, set and dried, the improvement which comprises using as the relaxer the hair relaxer composition of claim 1.

21. In the method of treating human hair with a no-base relaxer composition in which the relaxer is applied to the hair, the hair physically smoothed, rinsed, shampooed, set and dried, the improvement which comprises using as the relaxer the hair relaxer composition of claim 2.

* * * * *